(12) United States Patent
Park et al.

(10) Patent No.: US 10,175,173 B2
(45) Date of Patent: Jan. 8, 2019

(54) CHEMICAL ELEMENT ANALYSIS DEVICE AND METHOD FOR CONTAMINANTS IN LIQUID

(71) Applicant: GWANGJU INSTITUTE OF SCIENCE AND TECHNOLOGY, Gwangju (KR)

(72) Inventors: Ki Hong Park, Gwangju (KR); Gi Baek Kim, Gwangju (KR); Kyoung Woong Kim, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 15/531,069

(22) PCT Filed: Nov. 30, 2015

(86) PCT No.: PCT/KR2015/012911
§ 371 (c)(1),
(2) Date: May 26, 2017

(87) PCT Pub. No.: WO2016/085313
PCT Pub. Date: Jun. 2, 2016

(65) Prior Publication Data
US 2017/0322162 A1    Nov. 9, 2017

(30) Foreign Application Priority Data

Nov. 28, 2014   (KR) .................. 10-2014-0168248
Nov. 27, 2015   (KR) .................. 10-2015-0167638

(51) Int. Cl.
| | |
|---|---|
| *G01J 3/30* | (2006.01) |
| *G01N 21/71* | (2006.01) |
| *G01N 1/44* | (2006.01) |
| *G01N 1/40* | (2006.01) |

(52) U.S. Cl.
CPC ............ *G01N 21/718* (2013.01); *G01N 1/44* (2013.01); *G01N 2001/4027* (2013.01); *G01N 2001/4083* (2013.01); *G01N 2001/4088* (2013.01)

(58) Field of Classification Search
CPC ........ G01N 21/718; G01N 1/44; G01N 21/63; G01N 21/64; G01N 15/02; G01N 15/06
See application file for complete search history.

(56) References Cited

FOREIGN PATENT DOCUMENTS

| | | | | |
|---|---|---|---|---|
| JP | 62-239051 | 10/1987 | | |
| JP | 2005-221373 | 8/2005 | | |
| JP | 2005221373 A | * 8/2005 | ............. | G01N 21/63 |

(Continued)

*Primary Examiner* — Jamil Ahmed
(74) *Attorney, Agent, or Firm* — Mayer & Williams, PC; Stuart H. Mayer (57) ABSTRACT

The present invention relates to a chemical element analysis device and method for contaminants in a liquid. The chemical element analysis device for contaminants in a liquid according to the present invention comprises: a sample storage unit 10 for storing a sampled liquid sample 1; a laser unit 20 for emitting a laser beam 21: 21*a*, 21*b*, and 21*c* and irradiating the laser beam 21 to the sample 1: 1*a*, 1*b*, and 1*c* sprayed from the sample storage unit 10; and a spectrometer 30 for collecting plasma light 31: 31*a*, 31*b*, and 31*c* generated by irradiating the laser beam 21 to the sample 1, and measuring a spectrum of the plasma light 31.

22 Claims, 8 Drawing Sheets

(56) References Cited

FOREIGN PATENT DOCUMENTS

| KR | 1020070004715 | | | 1/2007 | |
|----|---------------|---|---|--------|---|
| KR | 20090049706 A | * | 5/2009 | ............ G01N 15/02 |
| KR | 1020090049706 | | | 5/2009 | |
| KR | 10201000080764 | | | 9/2010 | |
| KR | 1020130026204 | | | 3/2013 | |

* cited by examiner

Target elements in flowback water from shale gas fields

| No. | Element | Wavelength (nm) |
|---|---|---|
| 1 | Arsenic | 234.984, 274.50, 278.02, 286.04 |
| 2 | Barium | 455.403, 493.409, 614.172, 649.69, 413.066 |
| 3 | Calcium | 393.366, 396.847, 317.933, 373.687 |
| 4 | Chromium | 357.869, 283.563, 359.349, 425.435, 427.48 |
| 5 | Iron | 274.648, 274.948, 275.573, 259.94 |
| 6 | Magnesium | 279.553, 280.27, 383.829, 383.23 |
| 7 | Selenium | 203.984, 207.484, 241.347, 473.08, 473.897 |
| 8 | Boron | 249.677, 345.13, 206.665, 208.89 |
| 9 | Sodium | 589.593, 588.995, 330.237, 819.483 |
| 10 | Chloride | 837.594, 833.331, 822.174, 821.204 |
| 11 | Potassium | 766.49, 769.896, 404.721, 404.414 |

FIG. 10

Target elements in water (wastewater)

| No. | Element | Wavelength (nm) |
|---|---|---|
| 1 | Arsenic | 234.984, 274.50, 278.02, 286.04 |
| 2 | Cadmium | 508.582, 361,051, 479.991, 346.62, 361.287 |
| 3 | Chromium | 357.869, 283.563, 359.349, 425.435, 427.48 |
| 4 | Lead | 405.78, 373.994, 368.346, 357.273, 363.956 |
| 5 | Mercury | 435.832, 546.074, 365.015, 404.656, 313.155 |
| 6 | Selenium | 203.984, 207.484, 241.347, 473.08, 473.897 |
| 7 | Antimony | 259.805, 252.852, 326.751, 287.792, 276.995 |
| 8 | Barium | 455.403, 493.409, 614.172, 649.69, 413.066 |
| 9 | Beryllium | 313,042, 332.133, 265.062, 249.473, 234.861 |
| 10 | Boron | 249.677, 345.13, 206.665, 208.89 |
| 11 | Molybdenum | 386.411, 390.296, 379.825, 550.649, 281.615 |
| 12 | Nickel | 361.939, 341.476, 352.454, 310.155, 356.637 |
| 13 | Silver | 328.068, 338.289, 243.781, 241,323, 546.55 |
| 14 | Thallium | 535.05, 276.8 |
| 15 | Iodide | 516.12, 546.462, 549.694, 562,569, 543.583 |

FIG. 11

Target elements in mine wastewater

| No. | Element | Wavelength (nm) |
|---|---|---|
| 1 | Iron | 274.648, 274.948, 275.573, 259.94 |
| 2 | Nickel | 361.939, 341.476, 352.454, 310.155, 356.637 |
| 3 | Arsenic | 234.984, 274.50, 278.02, 286.04 |
| 4 | Manganese | 257.61, 259.373, 260.569, 294.92 |
| 5 | Lead | 405.78, 373.994, 368.346, 357.273, 363.956 |
| 6 | Cadmium | 508.582, 361,051, 479.991, 346.62, 361.287 |
| 7 | Copper | 324.754, 327.396, 521.82, 515.324 |
| 8 | Zinc | 481.053, 334.502, 330.258, 472.215 |
| 9 | Chromium | 357.869, 283.563, 359.349, 425.435, 427.48 |

FIG. 12

Target elements in radioactive wastewater

| No. | Element | Wavelength (nm) |
|---|---|---|
| 1 | Carbon | 247.856, 193.091, 833.515, 538.034 |
| 2 | Strontium | 430.545, 407.771, 416.18, 421.552 |
| 3 | Iodide | 516.12, 546.462, 549.694, 562,569, 543.583 |
| 4 | Cesium | 455.528, 794.388, 852.113, 459.317 |
| 5 | Plutonium (Pu) | 347.364, 347.657, 346.518, 345.611 |
| 6 | Krypton (Kr) | 810.4, 605.78 |
| 7 | Argon (Ar) | 763.5 |
| 8 | Xenon (Xe) | 823.2, 529.222 |

CHEMICAL ELEMENT ANALYSIS DEVICE AND METHOD FOR CONTAMINANTS IN LIQUID

TECHNICAL FIELD

The present invention relates to an apparatus and a method for performing elemental analysis of contaminants in a liquid. More particularly, the present invention relates to a portable apparatus and a method for performing elemental analysis of contaminants in a liquid, which is capable of directly analyzing the chemical elements of contaminants in a collected liquid sample on the spot.

BACKGROUND ART

In general, a liquid analysis apparatus is used to analyze the composition of various industrial process solutions for the purpose of quality control, pollution treatment, and so on. In particular, as the need for environmental protection has become increasingly important, it is important to analyze the components of liquid waste and treat them.

In general, according to a conventional liquid analysis apparatus/method, a predetermined amount of a target solution is sampled and transported to a desired place where an analysis apparatus is installed, then the transported sample solution is pretreated under conditions suitable for analysis, and then quantitative analysis can be done using a suitable analysis apparatus. However, in the case of using the conventional liquid analysis apparatus/method as described above, there is a problem that a complicated pretreatment process is performed, a long time is required for analysis, and it costs a lot of money to operate measurement devices. The disposal of large amounts of chemical reagents, which are essentially used, can also be a problem.

Meanwhile, due to the lack of conventional energy resources and rising oil prices, there has recently been a growing interest in shale gas, which is a non-conventional gas resource and a considerable amount of which is distributed across the world. In the past, production of shale gas was hard to make economic sense due to the problem of drilling technology, but the development of shale gas fields was accelerated with the development of hydraulic fracturing technology. Hydraulic fracturing technology is a technology that injects hydraulic fracturing fluid composed of water, sand and chemical additives under high pressure into the shale layer to cause cracks and to collect shale gas through the cracks.

When the hydraulic fracturing progresses or completes, the flowback water is treated. Since the chemical and oil added to the hydraulic fracturing fluid are included in the flowback water, the process of analyzing and treating the contaminants (contaminated materials) is necessarily carried out. Elemental analysis of these contaminants may utilize an Inductively Coupled Plasma (ICP) analysis method or an analysis method using Atomic Absorption Spectroscopy (AAS). However, even when a conventional analysis method such as ICP or AAS is used, the same problems as in the liquid analysis apparatus/method arise.

Accordingly, there is an urgent need for a solution to solve the problems accompanying the conventional liquid analysis apparatus/method.

DETAILED DESCRIPTION OF THE INVENTION

Technical Problem

Accordingly, the present invention has been made to solve the above problems accompanying the conventional technology, and it is an object of the present invention to provide a lightweight and portable apparatus and a method for performing elemental analysis of contaminants in a liquid, which is capable of directly analyzing chemical elements of contaminants in a collected liquid sample on the spot without the need of pretreatment.

It is another object of the present invention to provide an analysis apparatus and a method for performing elemental analysis of contaminants in a liquid, which is capable of analyzing solids remaining after evaporation of liquid by heating and drying a liquid sample and then concentrating the liquid sample.

Technical Solution

The above object of the present invention can be achieved by an apparatus for performing elemental analysis of contaminants in a liquid. The apparatus includes a sample storage unit for storing a sampled liquid sample; a laser unit for generating and irradiating a laser beam to the sample sprayed from the sample storage unit; and a spectrometer for collecting plasma light generated by the irradiation of the laser beam onto the sample and measuring a spectrum of the plasma light.

The sample storage unit may supply the sample the sample to at least one of a first supply unit and a second supply unit.

The sample storage unit may include a droplet spraying unit for atomizing the sample into droplets and spraying the sample into the first supply unit.

The apparatus may further include a main gas jetting unit for injecting an inert gas into the sample storage unit.

The apparatus may further include a first gas jetting unit for jetting an inert gas to the sample before the sample is sprayed from the end of the first supply unit.

The first supply unit may further include a pump for transporting the sample.

The apparatus may further include a membrane filter for filtering the sample before the sample is stored in the sample storage unit, wherein the membrane filter has a shape of a film and a filter hole for filtering the sample is formed on the surface of the membrane filter, thereby separating a particulate matter and an ionic material in the sample.

The second supply unit may spray the sample such that the sample is positioned on a transport plate.

The transport plate may be in the shape of a rotatable plate, and the sample sprayed from the second supply unit may be adsorbed and disposed on an upper surface of the transport plate, and the position of the sample may be moved such that the sample is irradiated with the laser beam as the transport plate rotates.

The transport plate may be in the shape of a plate having a predetermined length, and the sample may be adsorbed and disposed on an upper surface of the transport plate, and the position of the sample may be moved such that the sample is irradiated with the laser beam as the transport plate moves along the longitudinal direction.

A plurality of recessed placement holes may be formed on the upper surface of the transport plate so that the sample is adsorbed.

The apparatus may further include a heating unit disposed inside the transport plate or on a lower part of the transport plate, the heating unit may heat and dry the sample by applying heat to the transport plate.

The apparatus may further include a second gas jetting unit for jetting an inert gas to the sample irradiated with the laser beam.

The above object of the present invention can also be achieved by a method for performing elemental analysis of contaminants in a liquid. The method includes the steps of: (a) storing a sampled liquid sample; (b) spraying the stored sample and irradiating a laser beam onto the sample sprayed; and (c) collecting plasma light generated by the irradiation of the laser beam onto the sample and measuring a spectrum of the plasma light.

The sample may be atomized into droplets and sprayed, and a laser beam may be irradiated onto the sprayed sample.

An inert gas may be jetted to the stored sample.

An inert gas may be jetted to the sample before the sample is sprayed.

A particulate matter and an ionic material in the sample may be separated using a membrane filter before the sample is stored, and the membrane filter may have a shape of a film and a filter hole for filtering the sample may be formed on a surface of the membrane filter.

The sample may be sprayed so as to be adsorbed on an upper surface of the transport plate, and the position of the sample may be moved such that the sample is irradiated with the laser beam as the transport plate moves.

A plurality of recessed placement holes may be formed on the upper surface of the transport plate so that the sample is adsorbed.

The sample may be heated and dried by heating the transport plate with a heating unit disposed inside the transport plate or on a lower part of the transport plate.

An inert gas may be jetted to the sample irradiated with the laser beam.

Advantageous Effects

According to the present invention configured as described above, it is possible to provide a lightweight and portable apparatus and a method for performing elemental analysis of contaminants in a liquid, which is capable of directly analyzing chemical elements of contaminants in a collected liquid sample on the spot without the need of pretreatment.

In addition, according to the present invention, it is possible to analyze solids remaining after evaporation of liquid by heating and drying a liquid sample and then concentrating the liquid sample.

EXPLANATION OF REFERENCE NUMERALS 1, 1a, 1b, 1c: sample
5: injection port
10: sample storage unit
11: first supply unit
15: second supply unit
20: laser unit
21, 21a, 21b, 21c: laser beam
30: spectrometer
31, 31a, 31b, 31c: plasma light
40: controller
50: membrane filter
60: main gas jetting unit
70: first gas jetting unit
80: second gas jetting unit
90, 100: transport plate
95, 105: heating unit
102: placement hole

MODE OF THE INVENTION

The following detailed description of the invention refers to the accompanying drawings, which show, by way of illustration, specific embodiments in which the invention may be made. These embodiments are described in sufficient detail to enable those skilled in the art to make the invention. It will be understood that the various embodiments of the present invention are different, but need not be mutually exclusive. For example, certain features, structures, and characteristics described herein may be implemented in other embodiments without departing from the spirit and scope of the invention in connection with one embodiment. It is also to be understood that the position or arrangement of the individual elements within each disclosed embodiment may be changed without departing from the spirit and scope of the present invention. The following detailed description is, therefore, not to be taken in a limiting sense, and the scope of the present invention is defined by the appended claims, along with the full scope of equivalents of the claims, if properly explained. In the drawings, like reference numerals refer to the same or similar functions throughout the various views, and lengths and areas, thicknesses, and the like, as well as the shapes may be exaggerated for convenience.

Hereinafter, preferred embodiments of the present invention will be described in detail with reference to the accompanying drawings, so that those skilled in the art can easily carry out the present invention.

Figure 1:
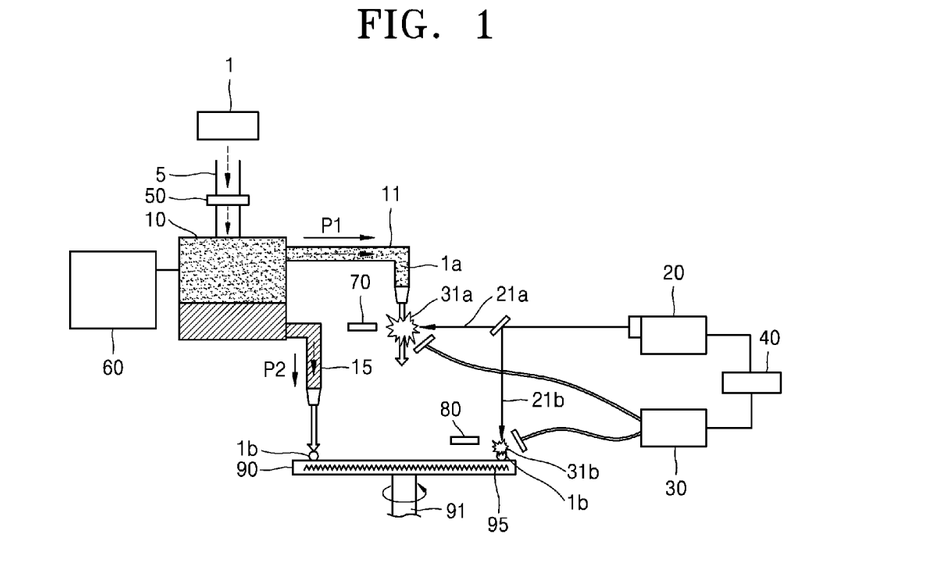
FIGS. 1 and 2 are schematic views of an apparatus for elemental analysis of contaminants in a liquid according to an embodiment of the present invention.
Figure 2:
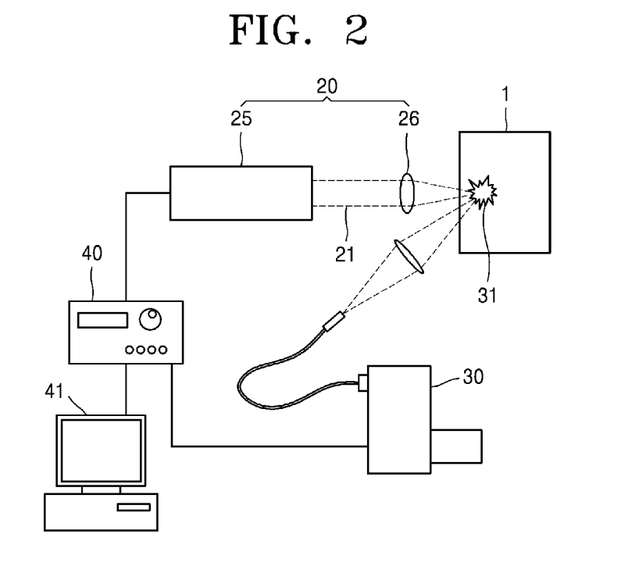

FIGS. 1 and 2 are schematic views of an apparatus for elemental analysis of contaminants in a liquid according to an embodiment of the present invention. The apparatus will be referred to as a liquid analysis apparatus in the following description.

Referring to FIG. 1, a liquid analysis apparatus according to an embodiment of the present invention includes a sample storage unit 10 for storing a sampled liquid sample 1; a laser unit 20 for generating and irradiating a laser beam 21: 21a, 21b and 21c to the sample 1: 1a, 1b and 1c sprayed from the sample storage unit 10 and a spectrometer 30 for collecting plasma light 31: 31a, 31b and 31c generated by the irradiation of the laser beam 21 onto the sample 1 and measuring a spectrum of the plasma light 31.

Referring to FIG. 2, the basic principle of the liquid analysis apparatus will be described below. The analysis of the sample 1 may utilize a spectroscopic analysis having plasma as an excitation source. The laser unit 20 is a device for generating and irradiating the laser beam 21 onto the sample 1. The laser unit 20 includes a laser generator 25 and a condenser lens 26. The laser beam 21 may be, for example, a high-power laser beam 21 such as a Nd:YAG laser. However, the laser beam 21 is not necessarily limited to the Nd:YAG laser. Here, the power of the laser beam 21 can be controlled by a controller 40. The laser beam 21 can be converged through the condenser lens 26 and irradiated onto the sample 1.

When the laser beam 21 is irradiated onto the sample 1, the sample 1 can be vaporized and separated into electrons and positive ions, thereby generating plasma. Plasma emits energy in the form of light as atoms and ions in the excitation state return to the ground state. Spectroscopic analysis of such plasma light enables a qualitative/quantitative analysis of elements.

In this way, the laser beam 21 is irradiated onto the sample 1 through the laser unit 20 of the liquid analysis apparatus according to the present invention, and the plasma light 31 generated at this time is subjected to spectroscopic analysis. Spectroscopic analysis of the plasma light 31 may be made by a spectrometer 30. The laser beam 21 may have a wavelength of 1064 nm. Furthermore, in order to reduce the spot size of the laser beam 21 irradiated, the focal length of the objective lens can be set to be reduced. The spot size of the laser beam may be 4 $\lambda f/\pi D$ (D: diameter of incident beam, f: focal length), and the spot size of the laser beam can be reduced by reducing the focal length f of the objective lens. Thus, even if the laser unit 20 generates a low intensity laser beam, the laser beam 21 can be irradiated having high intensity through integration. Accordingly, the minimized laser intensity may serve to minimize heat generation, thereby simplifying the structure of the laser unit 20 and reducing the weight of the product. As a result, a portable analysis apparatus having mobility may be designed.

The spectrometer 30 is a device for measuring a spectrum of the plasma light 31. When an element returns from its excited state to its ground state, the element emits light having certain wavelength depending on its kind and excited state. Therefore, by analyzing the spectrum of the wavelength, qualitative and quantitative analysis of the components of a material can be performed. According to this principle, elements (contaminants) in the sample 1 can be analyzed qualitatively and quantitatively by collecting the plasma light 31 using the spectrometer 30 and measuring the spectrum of the plasma light 31. Meanwhile, the results of interpretation of the spectrum may be displayed by a computer 41.

Referring again to FIG. 1, the sample 1 may be a liquid sample that is sampled from a flowback water generated during the drilling of shale gas fields, normal wastewater, mine wastewater (mine drainage), and radioactive wastewater, and any kind of liquid other than the above-mentioned wastewater can be employed as the sample 1. In particular, the flowback water generated during the drilling process in shale gas fields will be further described below.

The drilling of a shale gas field uses a hydraulic fracturing technology. The hydraulic fracturing technology is a technique that injects a hydraulic fracturing fluid under high pressure into a shale layer that is hardened with accumulated sands and muds, thereby generating cracks and collecting shale gas. Meanwhile, the fluid that is returned to the ground while the hydraulic fracturing is in progress or after it is completed, that is, the flowback water includes clay, dissolved metal ions, dissolved solids, suspended particles, and chemical additives added to the hydraulic fracturing fluid. Therefore, in the drilling process in the shale gas field, it is necessary to treat the flowback water containing contaminants such as heavy metals. Therefore, the liquid analysis apparatus of the present invention has been invented for the purpose of facilitating the water treatment by carrying out a real-time analysis of polluted materials such as flowback water, normal wastewater, mine wastewater, nuclear wastewater, etc. on the spot.

The sample 1 may be introduced through the injection port 5 of the liquid analysis apparatus and stored in the sample storage unit 10. The sample storage unit 10 is a space in which the liquid sample 1 is stored and may supply the sample 1 to at least one of a first supply unit 11 and a second supply unit 15.

Figure 3:
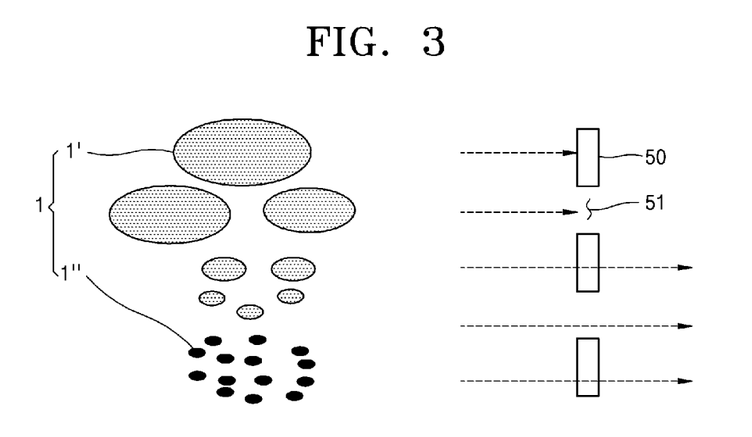
FIG. 3 is a cross-sectional view of the membrane filter shown in FIG. 1.

The sample 1 may be filtered by a membrane filter 50 before being stored in the sample storage unit 10. The membrane filter 50 is a thin film for filtering the substances in the sample 1 and serves as a filter. As shown in FIG. 3, the membrane filter 50 has a shape of a film, and a filter hole 51 for filtering the sample 1 is formed on the surface of the membrane filter 50, so that the particulate matter 1' and the ionic material 1" in the sample 1 is separated.

The substances in the sample 1 may be analyzed separately by using the membrane filter 50. Particularly, only the ionic material 1" can be analyzed separately by filtering the particulate matter 1' in the sample 1 using the membrane filter 50. Furthermore, it is possible to analyze the sample 1 containing the particulate matter 1' and the ionic material 1" without using the membrane filter 50. As described above, there is an advantage that the difference between the particulate matter 1' and the ionic material 1" can be confirmed by separating the particulate matter 1' and the ionic material 1" and analyzing them in a separate manner.

Depending on the diameter of the filter hole 51, the filtration is divided into microfiltration (MF) and ultrafiltration (UF) processes. Meanwhile, the membrane filter 50 may be a microfiltration membrane or an ultrafiltration membrane. Here, the type of the membrane filter 50 is determined in consideration of the diameter of the substances in the sample 1, the amount of the sample 1, the flow rate, cost, and the like. In view of these factors, microfiltration membranes are preferred, but the present invention is not necessarily limited thereto. Also, the membrane filter 50 is illustrated as being formed in the injection port 5, but it is not necessarily limited thereto and may be formed in the first and second supply units 11 and 15.

A main gas jetting unit 60 for injecting an inert gas into the sample storage unit 10 may be provided. The main gas jetting unit 60 may remove the air contained in the sample 1 by jetting an inert gas such as argon gas or helium gas to the sample 1 in the sample storage unit 10. Air contains gases such as oxygen, nitrogen, hydrogen, etc., which may affect the spectrum when plasma is generated. Therefore, the main gas jetting unit 60 may remove the air that may affect the spectrum by primarily jetting the substantially non-reactive inert gas to the sample 1 in the sample storage unit 10. Thus, the liquid analysis apparatus according to the present invention can provide greatly improved detection sensitivity and increased reproducibility of the results of analysis.

The first supply unit 11 is a pipe in the shape of a hollow tube. The sample 1a atomized in droplets is moved through the first supply unit 11 (P1: first process) and then sprayed through the nozzle at the end of the first supply unit 11. The sample 1a atomized in droplets may have a size of about 100 nm to several μm.

The sample storage unit 10 may include a droplet spraying unit (not shown) for atomizing the sample 1 into droplets and spraying the sample into the first supply unit 11. Here, the droplet spraying unit may include a nebulizer or an atomizer. The nebulizer is characterized in that the size of the droplet 1a is relatively larger than that of the atomizer, and that it is possible to detect ionic material and particulate matter at the same time. On the other hand, the atomizer has a feature that the size of the droplet 1a is small and that it is possible to minimize the influence of water during a drying process. Since the sample 1a sprayed by the droplet spraying unit does not undergo a separate drying process, it is preferable to use the nebulizer. However, the droplet spraying unit is not necessarily limited to the nebulizer, and the atomizer may be used depending on the substances in the sample 1.

A first gas jetting unit 70 may further be provided for jetting an inert gas to the sample 1a before the sample 1a is sprayed through the nozzle at the end of the first supply unit 11. The first gas jetting unit 70 jets an inert gas such as argon gas or helium gas to the sample 1a before the sample is sprayed through the nozzle at the end of the first supply unit 11, thereby secondarily removing the air from the sample 1a. Therefore, the liquid analysis apparatus according to the present invention may provide more improved detection sensitivity and more increased reproducibility of the results of analysis.

In order to smoothly transport the sample 1a, a pump (not shown) may be further provided in the first supply unit 11. The pump is preferably disposed at the distal end of the first supply unit 11 although the pump may be disposed anywhere in the first supply unit 11 as long as the pump provides a suction force for transporting the sample 1a.

The laser beam 21a is irradiated onto the sample 1a sprayed from the end of the first supply unit 11 and plasma is generated as the sample 1a is vaporized and separated into electrons and positive ions. The plasma emits plasma light 31a while returning to the ground state from the excited state. The plasma light 31a may be collected by the spectrometer 30 and the spectrum may be measured such that the elements are analyzed qualitatively/quantitatively. Since the plasma light 31a may be generated to have a wavelength of about 200 nm to about 900 nm, in order to prevent the detection efficiency from being deteriorated by chromatic aberration, a lens capable of preventing chromatic aberration may be used as the input lens (not shown) of the spectrometer 30 or a process of correcting chromatic aberration may further be carried out in the spectrometer 30. A controller 40 may control the power of the laser beam 21a, analyze the measurement results of the spectrometer 30 and display the results on the computer 41 (see FIG. 2).

The second supply unit 15 is a pipe in the shape of a hollow pipe like the first supply unit 11. However, the sample 1b itself in the liquid state instead of the sample 1a atomized in droplets is moved in the second supply unit 15. The sample 1b moved in the second supply unit 15 is not atomized into droplets by a nebulizer or an atomizer, but a nebulizer or an atomizer may be used as long as conversion into droplets having a diameter less than a predetermined diameter is required.

The movement of the sample 1b in the second supply unit 15 (P2: second process) may be employed when the threshold of the contaminant in the sample 1 is low. Meanwhile, when the degree of detection of the contaminant exceeds the reference value during a real-time monitoring of the first process P1, it is possible to switch to the second process P2 for more accurate measurement. When the concentration of the sample 1 is equal to or less than a predetermined concentration value and therefore measurement by the spectrometer 30 is impossible with the sample 1*a* moved (P1) in the first supply unit 11, it is possible to heat and dry the sample 1*b* sprayed from the second supply unit 15. The sample 1 containing a relatively large amount of water as compared with the contaminants has a low detection sensitivity and therefore a desired analytical value cannot be obtained even if the plasma light 31*a* of the sample 1*a* moved through the first supply unit 11 is analyzed. Therefore, the sample 1 is heated and dried to evaporate the water such that the concentration of the sample 1 is increased to a predetermined concentration value or more and then the analysis is carried out.

Meanwhile, the sample 1*b* moved (P2) through the second supply unit 15 can be sprayed so as to be positioned on the transport plate 90. A nozzle or a syringe may be provided at the end of the second supply unit 15 to spray the sample 1*b* with a suitable droplet size. The transport plate 90 is in the shape of a rotatable plate, and the sample 1*b* can be adsorbed and disposed on a surface (upper surface) of the transport plate.

A surface (upper surface) of the transport plate 90 may be subjected to a hydrophilic treatment. The hydrophilic treatment may be carried out using a method such as bonding a hydrophilic film coating or a hydrophilic filter to the transportation plate 90. In the liquid analysis using a conventional Al filter and the like, the sample is crystallized due to the salt and contaminants in the sample. Thus, it was problematic that the accuracy in analysis of the sample was low and consistent results were not obtained. However, according to the present invention, as the hydrophilic treatment is performed on the transport plate 90, the sample 1*b* can be easily adsorbed and disposed, and the sample 1*b* can be evenly distributed on the transport plate 90. Furthermore, it is possible to shorten the drying time of the sample 1*b* and to prevent the crystallization from proceeding after the sample 1*b* is dried. Therefore, high accuracy in analysis and consistent results can be achieved.

In addition, a plurality of recessed placement holes (not shown) may be formed on the upper surface of the transport plate 90 so that the sample 1*b* can be more stably adsorbed. The placement holes are fine holes formed such that the sample 1*b* is stably adsorbed to the transportation plate 90. Therefore, even when the transport plate 90 is moved, the sample 1*b* disposed on the transport plate 90 is less affected by vibration or impact. The transport plate 90 can be rotated by a rotating member 91 such as a motor connected to the lower portion.

When the transport plate 90 rotates, the sample 1*b* adsorbed and disposed on the transport plate 90 also moves and can be moved to a position where the laser beam 21*b* can be irradiated. The transport plate 90 may be made of a material that does not affect the plasma light 31*b* depending on the material in the sample 1*b*. For example, if the material in the sample 1*b* is a heavy metal, the transport plate may be made of nylon, or may be made of a metal when the material in the sample is a carbon compound. However, the transport plate 90 is not necessarily limited to such a material.

In order to heat and dry the sample 1, a heating unit 95 may be disposed inside the transportation plate 90, but a heating unit may be disposed on the lower part of the transportation plate 90. The heating unit 95 is a heating device for applying heat to the transportation plate 90. The heating unit 95 heats the sample 1b disposed on one side of the transportation plate 90 to evaporate the water. Here, the heating temperature of the heating unit 95 may be controlled by a control unit (not shown).

A second gas jetting unit 80 may further be provided for jetting an inert gas directly to the sample 1b irradiated with the laser beam 21b. The second gas jetting unit 80 corresponds to the above-described first gas jetting unit 70. However, the second gas jetting unit 80 directly jets an inert gas to the sample 1b and therefore is different from the first gas jetting unit 70 which jets an inert gas to the sample 1a before the sample 1a is irradiated with the laser beam 21a. This is for the purpose of more effectively removing the air from the sample 1b by jetting an inert gas when the laser beam is irradiated because the sample 1b is in contact with the air during the movement by the transport plate 90. Since the air contained in the sample 1b can be secondarily removed, the liquid analysis apparatus according to the present invention may provide more improved detection sensitivity and more increased reproducibility of the results of analysis.

The laser beam 21b is irradiated onto the sample 1b moved by the transport plate 90 and plasma may be generated as the sample 1b is vaporized and separated into electrons and positive ions. The plasma emits plasma light 31b while returning to the ground state from the excited state. The plasma light 31b may be collected by the spectrometer 30 and the spectrum may be measured such that the elements are analyzed qualitatively/quantitatively. The controller 40 may control the power of the laser beam 21b, analyze the measurement results of the spectrometer 30 and display them on the computer 41 (see FIG. 2).

Figure 4:
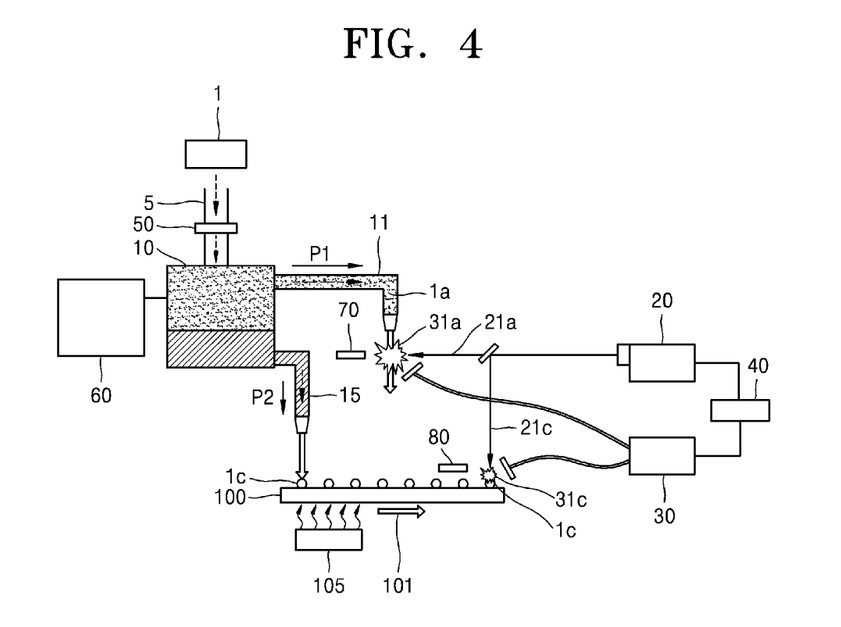
FIG. 4 is a partial schematic view of an apparatus for elemental analysis of contaminants in a liquid according to another embodiment of the present invention.
Figure 5:
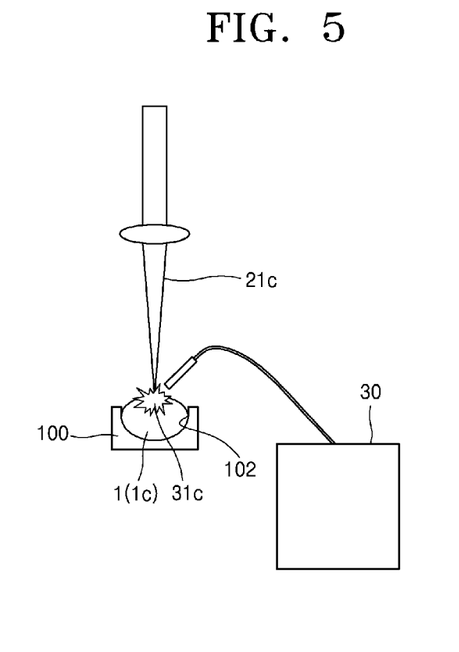
FIG. 5 is a front view of the transportation plate shown in FIG. 4.
Figure 6:
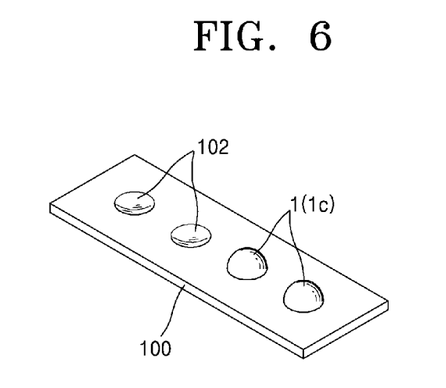
FIG. 6 is a perspective view of the transport plate shown in FIG. 4.

FIG. 4 is a partial schematic view of an apparatus for elemental analysis of contaminants in a liquid according to another embodiment of the present invention. FIG. 5 is a front view of the transportation plate shown in FIG. 4 and FIG. 6 is a perspective view of the transport plate shown in FIG. 4. The embodiment shown in FIGS. 4 to 6 differs from the embodiment shown in FIG. 1 only with regard to the configuration of the transport plate 100. Other components are the same so the description thereof is omitted.

Referring to FIGS. 4 to 6, the sample 1c moved through the second supply unit 15 may be sprayed so as to be positioned on the transport plate 100. The transport plate 100 is in the shape of a plate having a predetermined length, and the sample 1c can be adsorbed and disposed on a surface (upper surface) of the transport plate.

A hydrophilic treatment may be performed on a surface (upper surface) of the transport plate 100 so as to facilitate the adsorption.

A surface (upper surface) of the transport plate 100 may be subjected to a hydrophilic treatment. The hydrophilic treatment may be carried out using a method such as bonding a hydrophilic film coating or a hydrophilic filter to the transportation plate 100. As the hydrophilic treatment is added to the transport plate 100, the sample 1c can be easily adsorbed and disposed, and the sample 1c can be evenly distributed on the transport plate 100. Furthermore, it is possible to shorten the drying time of the sample 1c and to prevent the crystallization from proceeding after the sample 1c is dried. Therefore, high accuracy in analysis and consistent results can be achieved.

In addition, a plurality of recessed placement holes 102 may be formed on the upper surface of the transport plate 100 so that the sample 1c can be more stably adsorbed. The placement holes are fine holes formed such that the sample 1c is stably adsorbed to the transportation plate 100. Therefore, even when the transport plate 100 is moved, the sample 1c disposed on the transport plate 100 is less affected by vibration or impact.

Since the transport plate 100 moves along the longitudinal direction 101, the sample 1c disposed on the transport plate 100 can be moved to be irradiated with the laser beam 21c after being heated and dried. The transport plate 100 may be made of a material that does not affect the plasma light 31c depending on the material in the sample 1c. For example, if the material in the sample 1c is a heavy metal, the transport plate may be made of nylon, or may be made of a metal when the material in the sample is a carbon compound. However, the transport plate 100 is not necessarily limited to such a material.

In order to heat and dry the sample 1, a heating unit 105 may be disposed inside the transportation plate 100, but a heating unit may be disposed on the lower part of the transportation plate 100. The heating unit 105 is a heating device for applying heat to the transportation plate 100. The heating unit 105 heats the sample 1c disposed on one side of the transportation plate 100 to evaporate the water. Here, the heating temperature of the heating unit 105 may be controlled by a control unit (not shown).

The laser beam 21c is irradiated onto the sample 1c moved by the transport plate 100 and plasma may be generated as the sample 1c is vaporized and separated into electrons and positive ions. The plasma emits plasma light 31c while returning to the ground state from the excited state. The plasma light 31c may be collected by the spectrometer 30 and the spectrum may be measured such that the elements are analyzed qualitatively/quantitatively. The controller 40 may control the power of the laser beam 21c, analyze the measurement results of the spectrometer 30 and display them on the computer 41 (see FIG. 2).

As described above, the sampled liquid sample 1 can be directly injected into the liquid analysis apparatus of the present invention and then analyzed. It is not necessary to carry out a complicated pretreatment process and no chemical reagents are used. Furthermore, the liquid analysis apparatus is portable so that it is possible to directly analyze the components of the collected liquid sample 1 on the spot.

In addition, since the laser beam 21 is irradiated onto the sample 1 after the sample 1 is atomized and sprayed or heated and dried, the intensity of the laser beam to be used can be minimized (a laser beam 21 having an energy of 60 mJ/pulse and 200 mJ/pulse is used in the Experimental Example to be described with reference to FIG. 7). The minimized laser intensity may serve to minimize heat generation, thereby simplifying the structure of the laser unit 20 and reducing the weight of the product. As a result, a portable analysis apparatus having mobility may be designed.

The atomized sample 1a distributed by the nebulizer or the atomizer can be sprayed through the nozzle at the end of the first supply unit 11 without consideration of adjusting the size and amount of the droplets of the sample 1 in the sample storage unit 10, and therefore the droplets can be accumulated. In addition, by removing the air from the sample 1a by jetting the inert gas to the sample 1a, it is possible to increase the accumulation efficiency and to block the influence from the ambient air, thereby further improving the detection sensitivity.

When the concentration of the contaminant is low and therefore the threshold is low or when the degree of detection of the contaminant exceeds the reference value during a real-time monitoring, the liquid sample 1 is heated and dried to undergo a concentration process such that solids remaining after evaporation of liquid are analyzed. Thus, the concentration of the sample 1 can be increased and the detection sensitivity can be increased.

It is possible to perform both the quick and easy measurement using the first process P1 with the first supply unit 11 and the accurate measurement suing the second process P2 with the second supply unit 15. Furthermore, it is possible to improve the accuracy in analysis by presenting a result of complementing the result of analysis with the first supply unit 11 and the results of analysis with the second supply unit 15.

It is possible to automate the system by an analysis through the process in which the samples 1b and 1c are sprayed through the first and second supply units 11 and 15 from the sample storage unit 10 and the process in which the samples 1b and 1c are moved on the transportation units 90 and 100 and the heating units 95 and 105.

EXPERIMENTAL EXAMPLE

Hereinafter, the results of experiments using the liquid analysis apparatus of the present invention will be described.

Figure 7:
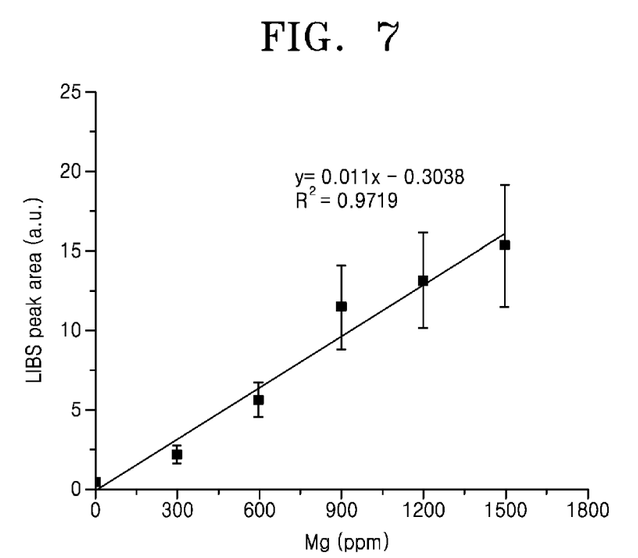
FIGS. 7 and 8 are graphs showing the results of measurement according to an embodiment of the present invention.
Figure 8:
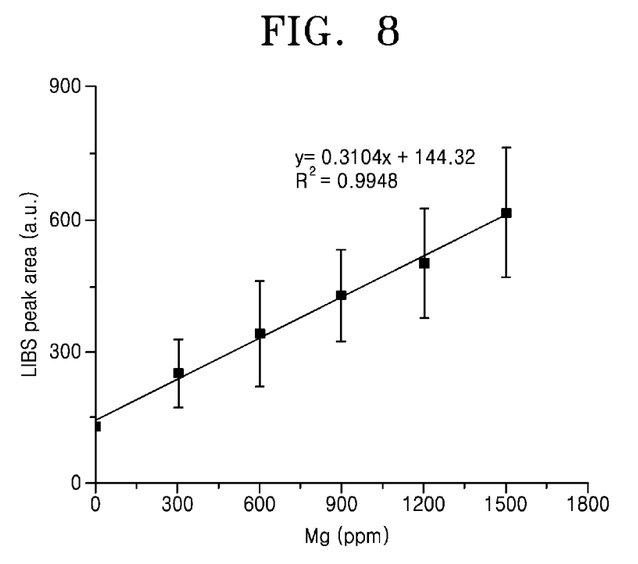
Figure 9:
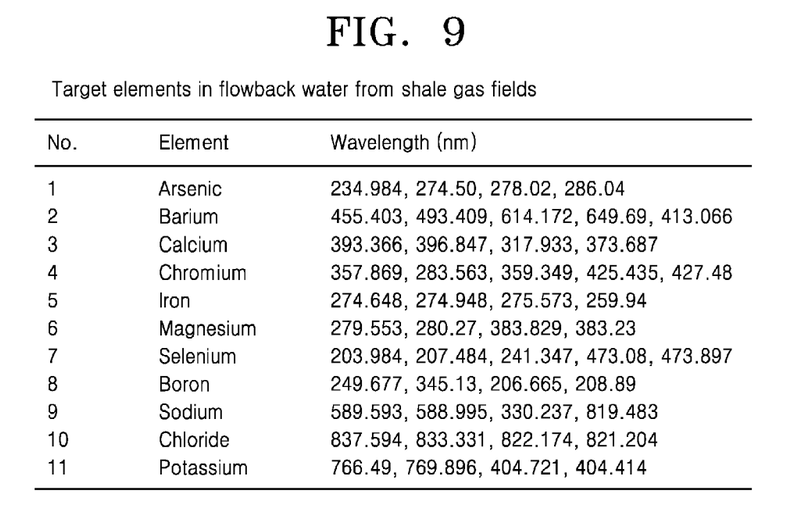
FIGS. 9 to 12 are tables showing the detected wavelengths of target elements for various liquid samples.
Figure 10:
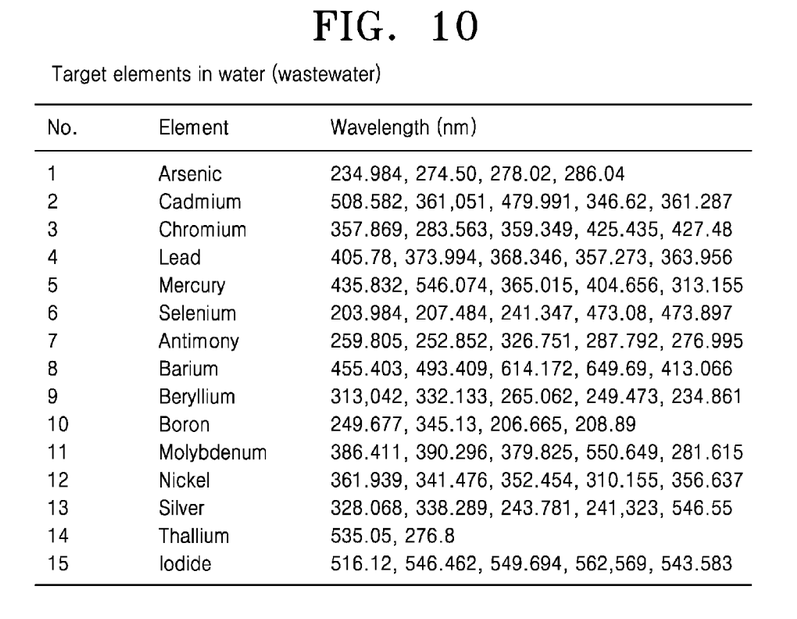
Figure 11:
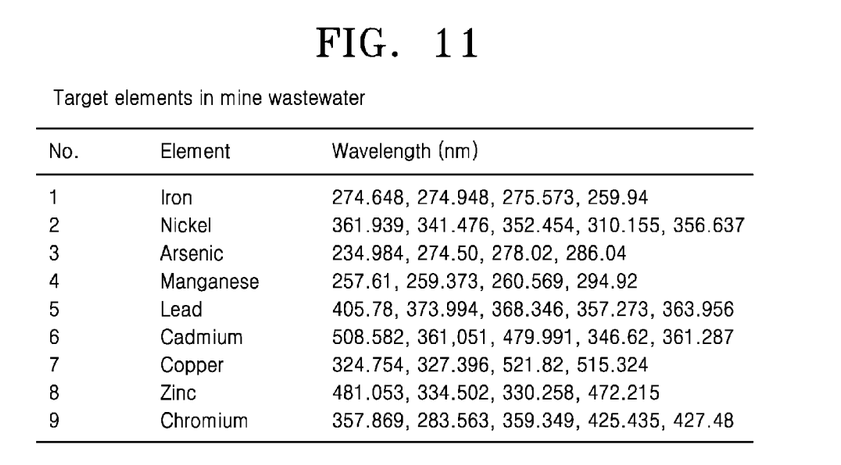
Figure 12:
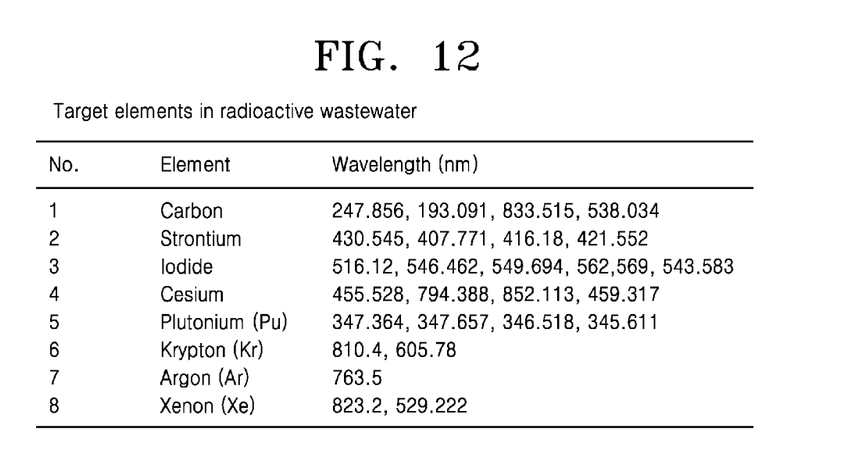

FIGS. 7 and 8 are graphs showing the results of measurement according to an embodiment of the present invention. The numerical value of Mg contained in the same liquid sample 1 was analyzed, FIG. 7 shows the result of analyzing the plasma light 31a by irradiating the laser beam 21a onto the sample 1a atomized in droplets through the first supply unit 11, and FIG. 8 shows the result of analyzing the plasma light 31b and 31c by irradiating the laser beam 21b and 21c onto the sample 1b after the sample 1b sprayed through the second supply unit 15 was heated and dried on the transport plates 95 and 105.

In the case shown in FIG. 7, a laser beam of 200 mJ/pulse was applied and in the case of FIG. 8, the transport plates 95 and 105 were covered with a hydrophilic filter (filter paper 53 (HYUNDAI MICRO), diameter 110 mm, pore size 1 μm to 2 μm) and then heated and dried at 70° C. for 10 minutes, and then irradiated with a laser beam of 60 mJ/pulse. In FIGS. 7 and 8, as the amount (ppm) of Mg increased, the peak area of the Laser Induced Breakdown Spectroscopy (LIBS) rose and the linearity ($R^2$) was 0.9719 and 0.9948, which is close to 1. In particular, in the case of FIG. 8, in which the concentration of the contaminant was increased by heating and drying the water, the linearity was higher and it was possible to carry out the analysis using a laser beam having a relatively low energy.

Therefore, it was confirmed that the liquid analysis apparatus of the present invention also provided highly reliable results of analysis, and that real-time analysis was possible on the spot with the highly portable liquid analysis apparatus.

FIGS. 9 to 12 are tables showing the detected wavelengths of target elements for various liquid samples. It is advantageous that it is possible to measure the spectrum of target elements in a liquid sample sampled from a flowback water from shale gas fields, normal wastewater, mine wastewater (mine drainage), and radioactive wastewater, thereby analyzing the substances qualitatively/quantitatively.

Figure 13:
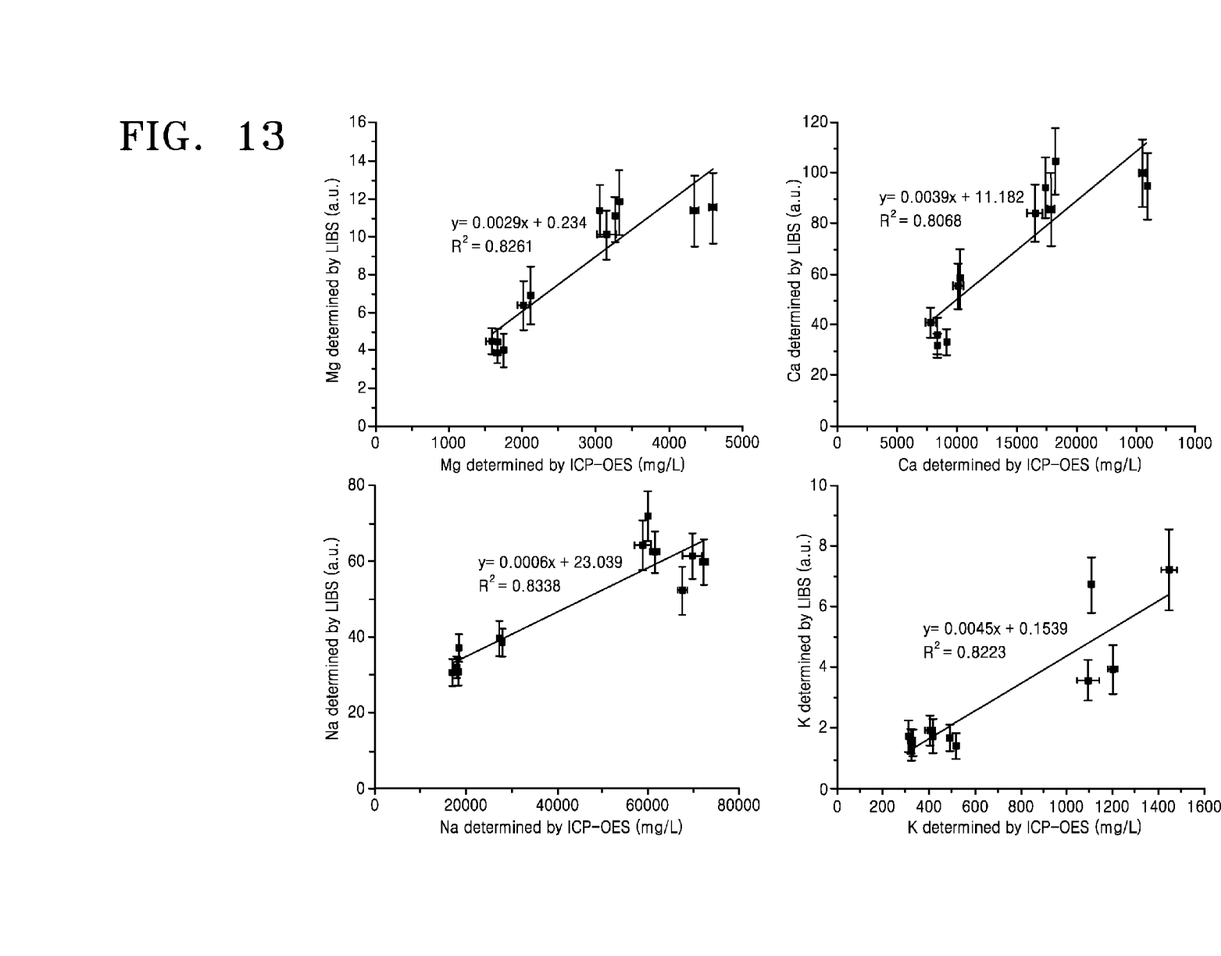
FIG. 13 is a table showing the results of elemental analysis using Inductively Coupled Plasma Optical Emission Spectrometer (ICP-OES) and Laser Induced Breakdown Spectroscopy (LIBS) through a first process according to an embodiment of the present invention.

FIG. 13 is a table showing the results of elemental analysis using Inductively Coupled Plasma Optical Emission Spectrometer (ICP-OES) and Laser Induced Breakdown Spectroscopy (LIBS) through a first process according to an embodiment of the present invention.

The X-axis of FIG. 13 shows the concentration of the target element in the sample through the ICP-OES and the Y-axis is the measurement value of the target element in the sample through the liquid analysis apparatus (LIBS) of the present invention which shows the results of analysis in which the laser beam 21a was directly irradiated onto the sample 1a sprayed from the first supply unit 11.

A sample 1 sampled from flowback water from shale gas fields was analyzed, a laser beam 21a of 200 mJ/pulse was irradiated with a delay time of 1 μs, and LIBS2000+ spectrometer was used as the spectrometer 30.

The linearity ($R^2$) of the data of ICP-OES and LIBS for Mg, Ca, Na, and K in the samples was 0.8261, 0.8068, 0.8338 and 0.8233, respectively, all of which are substantially close to 1. As a result, it was confirmed that the results of analysis of the LIBS of the present invention was at a reliable level when compared with the results of analysis of ICP-OES, which is a standard method for analyzing components in a sample.

Figure 14:
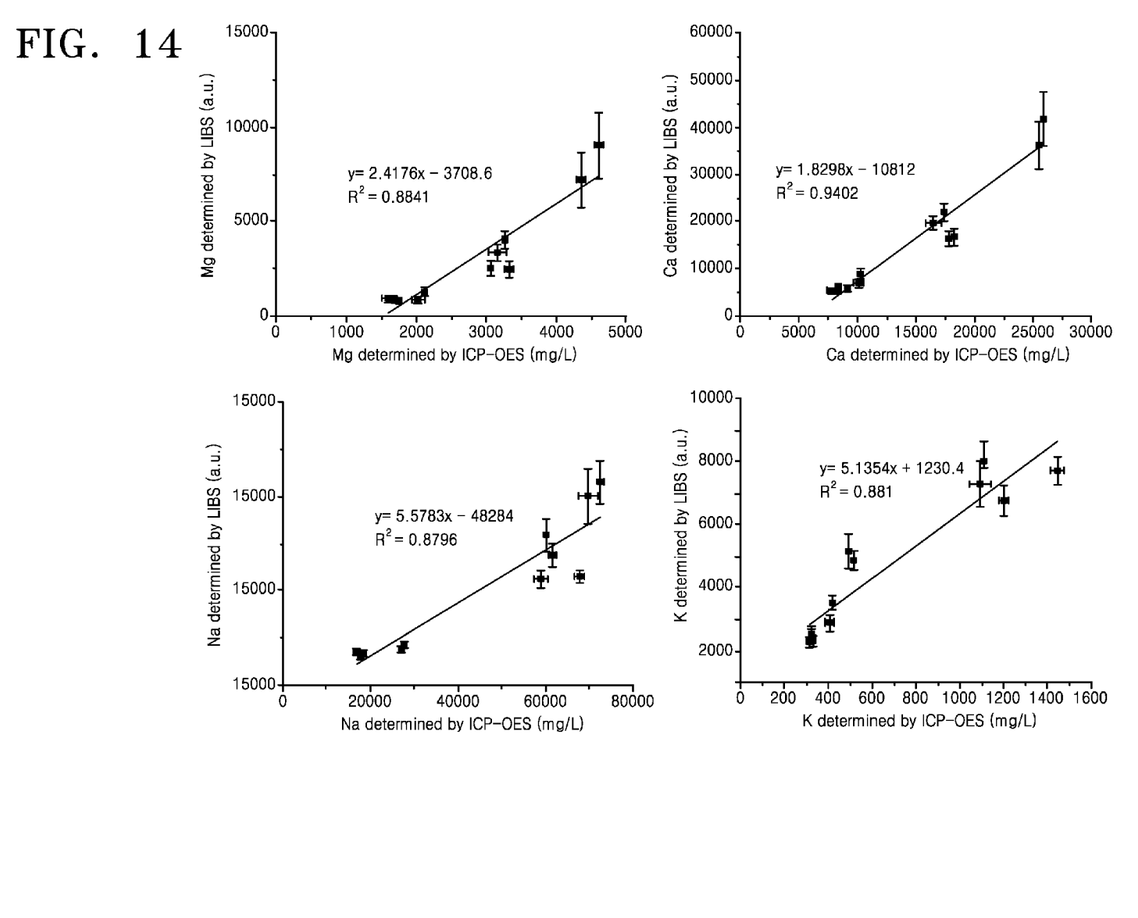
FIG. 14 is a table showing the results of elemental analysis using ICP-OES and LIBS through a second process according to an embodiment of the present invention.

FIG. 14 is a table showing the results of elemental analysis using ICP-OES and LIBS through a second process according to an embodiment of the present invention.

The X-axis of FIG. 14 shows the concentration of the target element in the sample through the ICP-OES and the Y-axis is the measurement value of the target element in the sample through the liquid analysis apparatus (LIBS) of the present invention which shows the results of analysis in which the laser beam 21b and 21c was irradiated onto the samples 1b and 1c after the samples 1b and 1c sprayed from the second supply unit 15 were heated and dried on the transport plates 90 and 100.

A sample 1 sampled from flowback water from shale gas fields was analyzed, a laser beam 21b of 600 mJ/pulse was irradiated with a delay time of 1 μs, and LIBS2000+ spectrometer was used as the spectrometer 30. The second process P2 is advantageous in that the laser beam 21b having a relatively low energy can be used since the heating and drying process of the sample is added. A hydrophilic filter was bonded onto the transport plates 90 and 100 to adsorb and place the samples 1b and 1c, and the samples 1b and 1c were then heated and dried at 70° C. for 10 minutes.

The linearity ($R^2$) of the data of ICP-OES and LIBS for Mg, Ca, Na, and K in the samples was 0.8841, 0.9402, 0.8796 and 0.8810, respectively, all of which are substantially close to 1. Since the analysis was carried out by concentrating the sample, the numerical value was closer to 1 than the result of the first process P1. As a result, it was confirmed that the results of analysis of the LIBS of the present invention was at substantially the same level as the results of analysis of ICP-OES, which is a standard method for analyzing components in a sample.

Referring to FIGS. 13 and 14, it was confirmed that the liquid analysis apparatus of the present invention also provided highly reliable results of analysis, and that real-time analysis was possible on the spot with the highly portable liquid analysis apparatus.

While the present invention has been particularly shown and described with reference to exemplary embodiments thereof, the present invention should not be limited to the above embodiments. Modifications and changes can be made by a person having ordinary skill in the art without departing from the spirit and scope of the present invention. Such modifications and changes are to be regarded as being within the scope of the invention and the appended claims.

The invention claimed is:

1. An apparatus for performing analysis of contaminants in a liquid, the apparatus comprising:
a sample storage unit for storing a sampled sample;

a first supply unit for receiving the sample from the sample storage unit;

a second supply unit for receiving the sample from the sample storage unit, under a predetermined condition;

a droplet spraying unit disposed in the sample storage unit and for atomizing the sample into droplets and supplying the sample into the first supply unit;

a transport plate disposed below the second supply unit and for heating and drying the sample;

a laser unit for irradiating a laser beam to the sample; and a spectrometer for measuring a spectrum of plasma light generated by the laser beam irradiated to the sample, wherein a laser beam is irradiated to the atomized sample supplied from the first supply unit such that the contaminants in the sample are analyzed, and wherein, under the predetermined condition, the sample is supplied from the second supply unit and then disposed on the transport plate to be heated and dried, and then the heated and dried sample is irradiated with a laser beam such that the contaminants in the sample are analyzed.

2. The apparatus according to claim 1, wherein wherein the predetermined condition is a case where the concentration of the contaminants in the sample is detected to be lower than the detection limit, or a case where the degree of detection of the contaminants in the sample exceeds the reference range.

3. The apparatus according to claim 1, further comprising: a main gas jetting unit for injecting an inert gas into the sample storage unit.

4. The apparatus according to claim 1, further comprising: a first gas jetting unit for jetting an inert gas to the sample in first supply unit.

5. The apparatus according to claim 1, wherein the first supply unit further comprises a pump for transporting a sample.

6. The apparatus according to claim 1, further comprising: a membrane filter for filtering the sample before a sample is stored in the sample storage unit, wherein the membrane filter has a shape of a film and a filter hole for filtering the sample is formed on the surface of the membrane filter, thereby separating a particulate matter and an ionic material in the sample.

7. The apparatus according to claim 1, wherein a hydrophilic treatment is performed on at least one surface of the transport plate.

8. The apparatus according to claim 1, wherein the transport plate is in the shape of a rotatable plate, and the sample supplied from the second supply unit is adsorbed and disposed on an upper surface of the transport plate, and wherein the position of the sample is moved such that the sample is irradiated with a laser beam as the transport plate rotates.

9. The apparatus according to claim 1, wherein the transport plate is in the shape of a plate having a predetermined length, and the sample supplied from the second supply unit is adsorbed and disposed on an upper surface of the transport plate, and wherein the position of the sample is moved such that the sample is irradiated with a laser beam as the transport plate moves along the longitudinal direction.

10. The apparatus according to claim 1, wherein a plurality of recessed placement holes is formed on the upper surface of the transport plate so that the sample is disposed.

11. The apparatus according to claim 1, further comprising a heating unit disposed inside or below the transport plate, wherein the heating unit dries the sample disposed on the transport plate by applying heat to the sample.

12. The apparatus according to claim 1, further comprising a second gas jetting unit for jetting an inert gas to the sample disposed on the transport plate.

13. A method for performing analysis of contaminants in a liquid using the apparatus according to claim 1, wherein a laser beam is irradiated to the atomized sample supplied from the first supply unit such that the contaminants in the sample are analyzed, and wherein, under the predetermined condition, the sample is supplied from the second supply unit and then disposed on the transport plate to be heated and dried, and then the heated and dried sample is irradiated with a laser beam such that the contaminants in the sample are analyzed.

14. The method according to claim 13, wherein the predetermined condition is a case where the concentration of the contaminants in the sample is detected to be lower than the detection limit, or a case where the degree of detection of the contaminants in the sample exceeds the reference range.

15. The method according to claim 13, wherein an inert gas is jetted to the sample stored in the sample storage unit.

16. The method according to claim 13, wherein an inert gas is jetted to the sample in the sample storage unit.

17. The method according to claim 13, wherein a particulate matter and an ionic material in the sample is separated using a membrane filter before the sample is stored in the sample storage unit, and wherein the membrane filter has a shape of a film and a filter hole for filtering the sample is formed on a surface of the membrane filter.

18. The method according to claim 13, wherein the position of the sample is moved such that the sample is irradiated with a laser beam as the transport plate moves.

19. The method according to claim 13, wherein a hydrophilic treatment is performed on at least one surface of the transport plate.

20. The method according to claim 13, wherein a plurality of recessed placement holes is formed on the upper surface of the transport plate so that the sample is disposed.

21. The method according to claim 13, wherein the sample disposed on the transport plate is heated and dried by heating the transport plate with a heating unit disposed inside or below the transport plate.

22. The method according to claim 13, wherein an inert gas is jetted to the sample disposed on the transport plate.

* * * * *